(12) United States Patent
Darbouret et al.

(10) Patent No.: US 6,472,159 B1
(45) Date of Patent: Oct. 29, 2002

(54) USE OF AN AMPHIPATHIC COMPOUND FOR PROVIDING AN ADJUVANT TO A SUBUNIT VACCINE

(75) Inventors: Anne Darbouret, Saint Maurice sur Dargoire (FR); Florence Brunel, Genay (FR); Jorge Ronco, La Mulatière (FR)

(73) Assignee: Aventis Pasteur S.A. (FR)

( * ) Notice: Subject to any disclaimer, the term of this patent is extended or adjusted under 35 U.S.C. 154(b) by 0 days.

(21) Appl. No.: 09/720,863

(22) PCT Filed: Jul. 2, 1999

(86) PCT No.: PCT/FR99/01604
§ 371 (c)(1),
(2), (4) Date: Apr. 16, 2001

(87) PCT Pub. No.: WO00/01345
PCT Pub. Date: Jan. 13, 2000

(30) Foreign Application Priority Data

Jul. 3, 1998 (FR) .............................................. 98 08700

(51) Int. Cl.[7] .......................... G01N 33/53; C12Q 1/70; A61K 39/42; A61K 39/00

(52) U.S. Cl. ......................... 435/7.1; 435/5; 424/149.1; 424/184.1

(58) Field of Search ................... 435/5, 7.1; 424/149.1, 424/184.1

(56) References Cited

U.S. PATENT DOCUMENTS 5,283,185 A 2/1994 Epand et al. ............ 435/172.3

FOREIGN PATENT DOCUMENTS

| CA | 1306689 | 12/1987 |
| WO | WO9640067 | 12/1996 |

*Primary Examiner*—Hankyel T. Park
(74) *Attorney, Agent, or Firm*—McDonnell Boehnen Hulbert & Berghoff

(57) ABSTRACT

The present invention provides a method of inducing an immune response to a subunit antigen in a non-responding subject by administering to the subject a composition comprising the subunit antigen and an amphipathic compound. A preferred antigen is a hepatitis B antigen, and a preferred amphipathic compound is DC-chol.

13 Claims, 2 Drawing Sheets

USE OF AN AMPHIPATHIC COMPOUND FOR PROVIDING AN ADJUVANT TO A SUBUNIT VACCINE

The invention relates to the field of vaccine adjuvants. In particular, the invention relates to the use of an amphipathic compound for the manufacture of a vaccine composition intended for nonresponding subjects.

It is known that, when a population of individuals is vaccinated against a disease, a number of them do not "respond" to the vaccination, that is to say that their immune system does not appear to react to the antigen administered. This problem is substantial to a greater or lesser degree depending on the diseases and the populations involved, but vaccine manufacturers are still trying to reduce, for each of the vaccines which they make available to doctors, the number of subjects likely to be "nonresponders". This problem is considered particularly for vaccines comprising purified antigens such as subunit vaccines produced by genetic engineering and in particular the hepatitis vaccine; however, while a number of amphipathic compounds, and in particular 3-β-[N-(N',N'-dimethylaminoethane)carbamoyl] cholesterol, commonly called DC-chol, are known which make it possible to increase the immune response in subjects who are already "responders", and are therefore considered to be good vaccine adjuvants, it is more difficult to find means of overcoming the problem of nonresponders, all the more so since all the reasons why an individual is a nonresponder have not yet been clearly identified. The research studies carried out in this field have shown that it was not possible to extrapolate the results obtained with adjuvants capable of increasing the immune response in "responding" subjects to the "nonresponding" subjects, given that some good adjuvants in responding subjects are found to have no effect in nonresponding subjects.

The aim of the invention is therefore to provide an improved vaccine as regards the level of seroconversion which it makes possible to obtain. For that, the invention proposes the use of an amphipathic compound for the preparation of a vaccine composition comprising at least one subunit antigen intended to be administered to target populations comprising individuals who are "nonresponders" to said antigen.

Figure 1:
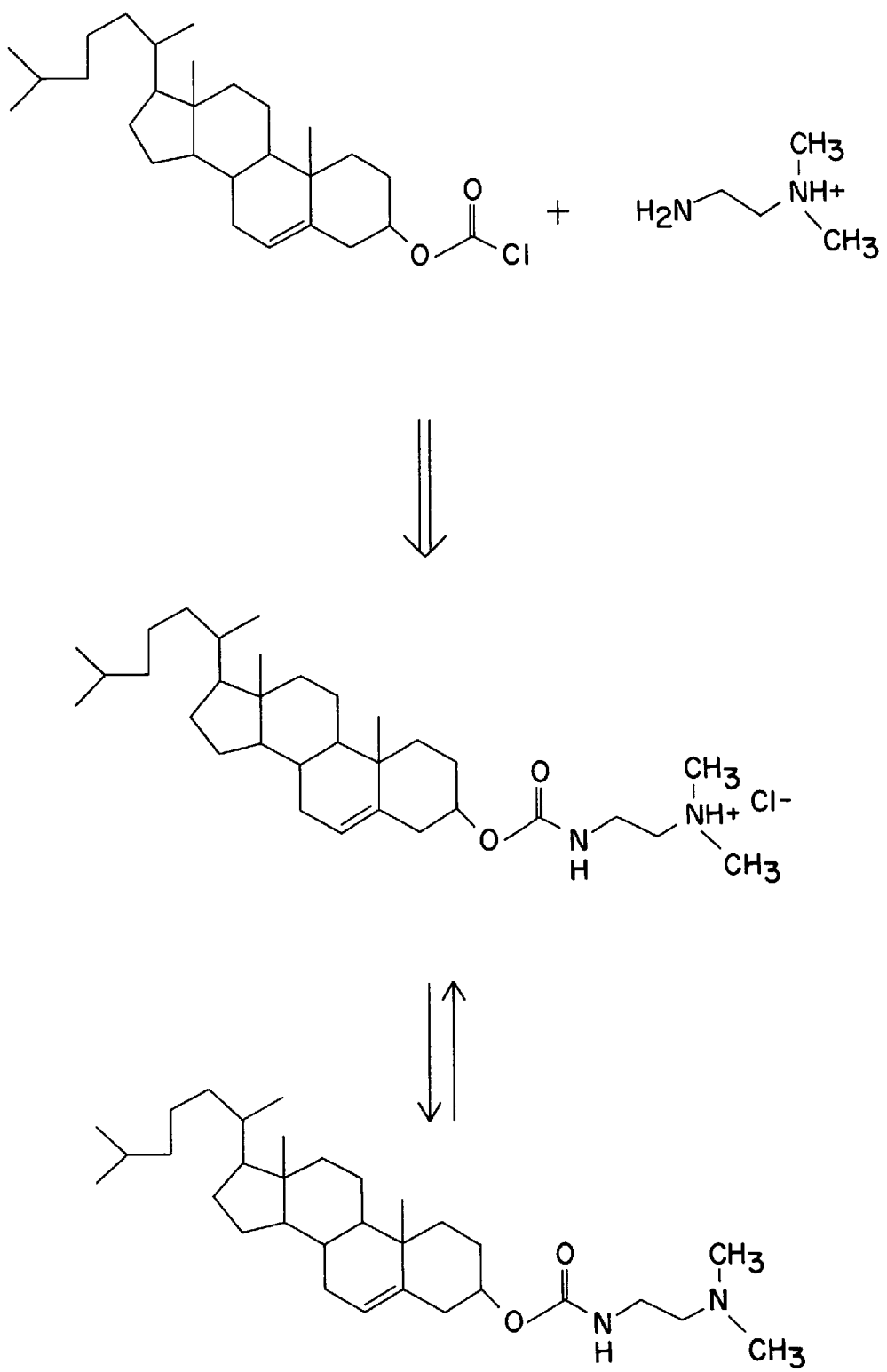

According to the invention, the amphipathic compounds are cholesterol derivatives attached to a quaternary ammonium or to a protonable amine by a carbamoyl bond. These compounds, such as DC-chol, can exist in the basic form, in the salt form or alternatively, and this is the most frequent case, in both of the two forms in equilibrium in a mixture, the shifting of the equilibrium toward either form depending on the composition of the mixture and in particular on its pH. One of the particularly advantageous amphipathic compounds for the purposes of the invention is DC-chol which may be obtained from cholesteryl chloroformate and from N,N-dimethylethylenediamine, according to the method described in patent U.S. Pat. No. 5,283,185 or, preferably, according to the method described in Example 8 of patent application WO 96/40067. The 2 forms of DC-chol generally in equilibrium are illustrated in FIG. 1. It is also possible to use a product obtained by reacting cholesteryl chloroformate and N,N,N-trimethylethylenediamine.

The amphipathic compounds may exist in the form of a dispersion in an aqueous or oily medium.

The vaccine composition which needs to be modified so as to reduce the number of individuals who are nonresponders thereto is a composition comprising at least one highly purified subunit antigen. Indeed, such antigens are in general less immunogenic than less purified preparations obtained from whole microorganisms and may therefore lead to a higher proportion of nonresponders. In particular, according to the invention, the number of nonresponders to the hepatitis B antigen is reduced. This may be any hepatitis B antigen, and in particular an antigen containing the S and pre-$S_2$ regions, such as the antigen described in patent EP 0 273 811.

To assess the efficacy of the subject of the invention, animal models are used. The results obtained with the compounds according to the invention and those obtained with conventional prior art adjuvants are thus compared in parallel on a group of nonsyngenic OF 1 mice which, like the human population, is composed of both responding subjects and nonresponding subjects. Comparison of the number of subjects to have undergone seroconversion in each of the groups makes it possible to assess the benefit of the subject of the invention.

Another test may be performed on mice belonging to a strain described as being a nonresponder to the antigen considered, such as the B10.MH$^{2f}$ mice for the hepatitis B antigen. Comparison of the results obtained in each of the groups makes it possible to assess the efficacy of the subject of the invention.

The vaccine composition according to the invention may be provided in liquid form or in freeze-dried form.

The vaccine composition according to the invention may be a monovalent composition (that is to say which is intended to protect against only one disease) or a multivalent composition (which protects against several diseases).

It may comprise, in addition to the adjuvant according to the invention, one or more other adjuvants conventionally intended to increase the response of the immune system, whether this is a humoral-type or a cellular-type response, or a combination of both types.

Conventionally, the vaccine composition according to the invention may comprise, in addition, all the ingredients usually present in vaccines: stabilizer, preservative, cryoprotectant and the like. This composition may be provided in liquid form or in freeze-dried form.

The following examples illustrate an embodiment of the invention.

Figure 2:
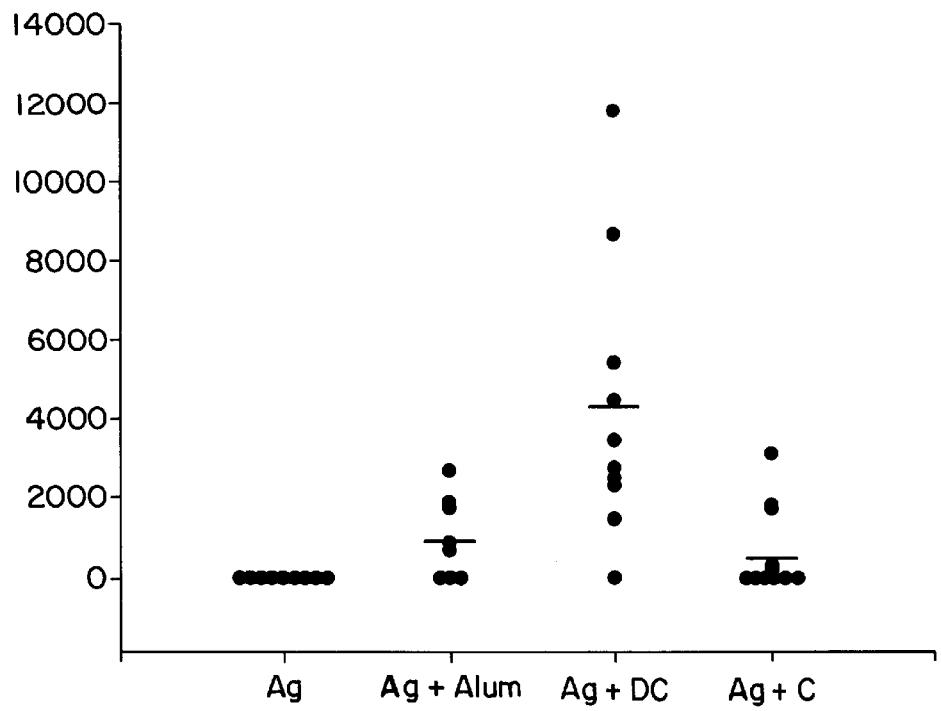
Figure 3:
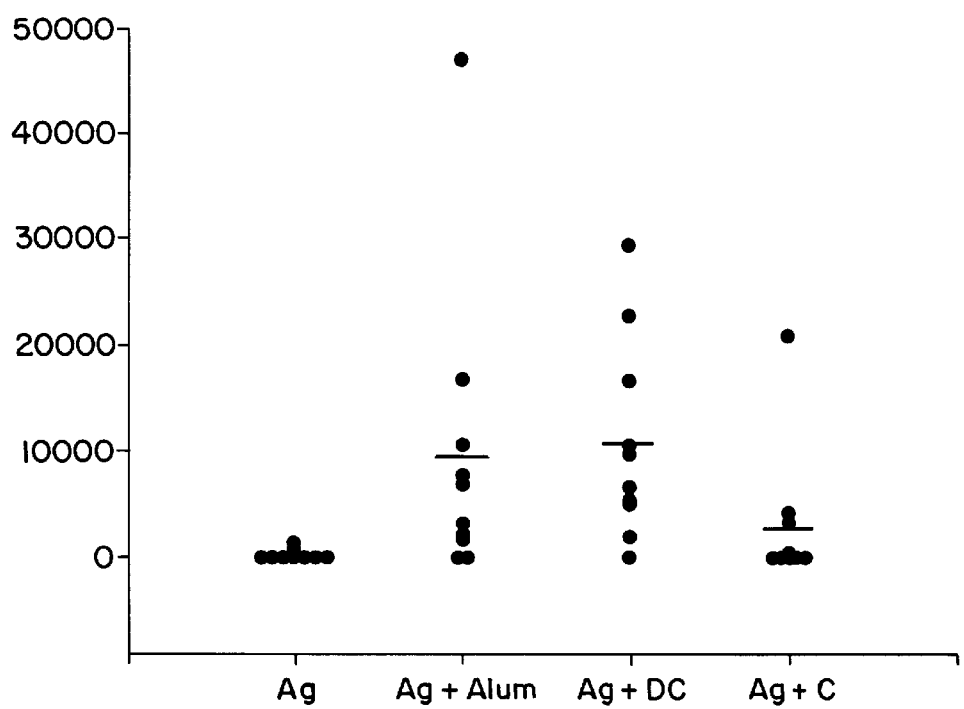

FIG. 1 represents the reaction for producing DC-chol.
FIGS. 2 and 3 illustrate the results obtained in Example 2.

EXAMPLE 1

Preparation of the Compositions for Immunization

A suspension of hepatitis B antigen is prepared according to the method described in patent EP 0 273 811, with the exception of the addition of aluminum hydroxide. This is therefore a suspension containing 4 mg/l of antigen in 1 mM phosphate buffer at pH 6.8. This suspension is called Suspension A.

DC-chol powder obtained according to the mode of preparation described in Example 8 of patent application WO 96/40067 is available. This powder is suspended in 20 mM Tris/HCl buffer containing 150 mM NaCl at pH 6.8, under nitrogen at 4° C. while the stirring is maintained for 48 h. A suspension containing 2 g/l of DC-chol is thus obtained.

By mixing these 2 suspensions volume for volume, a vaccine composition according to the invention is obtained which is divided into 0.5 ml doses, each comprising 1 µg of antigen against hepatitis B and 0.5 mg of DC-chol.

A new immunizing composition comprising, this time, 1 µg of antigen and 1 mg of aluminum hydroxide per 0.5 ml dose is prepared by adding aluminum hydroxide (Alhydrogel® provided by the company SUPERFOS BIOSECTOR) to suspension A.

A new composition for immunization is prepared from suspension A to which a prior art adjuvant C is added in order to obtain per 0.5 ml dose a quantity of antigen so 1 μg and a quantity of adjuvant of 0.5 mg. The nature and the dose of the prior art adjuvant were selected during comparative immunization trials against hepatitis B in BALB/C mice, by the subcutaneous route. The adjuvant selected is that which, during these trials, showed a high capacity to increase the humoral response of the antigen considered, the results obtained with this adjuvant being considerably superior to those obtained with aluminum hydroxide or with DC-chol.

EXAMPLE 2

Immunization of OF1 Mice

There are 4 groups of 10 nonsyngenic OF1 female mice, 6 to 8 weeks old, which represent a heterogeneous population reflecting the variability in the human population.

Each group of mice is immunized with a different vaccine composition:
- a $1^{st}$ group is immunized with 0.5 ml doses of the suspension A mentioned in Example 1, and therefore containing only the hepatitis B antigen
- a second group is immunized with 0.5 ml doses each comprising the hepatitis B antigen and aluminum hydroxide
- a third group is immunized with 0.5 ml doses each comprising the hepatitis B antigen and a prior art adjuvant
- a fourth group is immunized with 0.5 ml doses of the vaccine composition according to the invention.

The mice are immunized by the subcutaneous route, one to two hours after the preparation of the immunizing compositions.

Three weeks after the first immunization, blood is collected for assaying, and a second injection is carried out under the same conditions as the first. A second blood sample is collected three weeks after the second injection. All the blood samples are coagulated and centrifuged; the serum harvested is stored at −20° C. up to titration which s carried out by an ELISA technique.

The results obtained for each of the groups of mice are illustrated in FIG. 2 which indicates, in arbitrary ELISA units, the geometric mean antibody titers (GMT) obtained with each of the compositions tested after the $1_{st}$ injection, and in FIG. 3 which indicates the GMT means obtained after the booster injection.

It will thus be noted that, from the first injection, there is no nonresponding subject in the group of mice which received the vaccine composition according to the invention, whereas the use of the prior art adjuvant, which is nevertheless capable of substantially increasing the immune response in mice which are already "responders", does not make it possible, even after the booster injection, to make all the subjects "responders".

EXAMPLE 3

Immunization of B10.MH$^{2f}$ Mice

The 4 preparations for immunization described in Example 2 are available which are administered, this time, to 4 groups of 8 B10.M mice which are mice described as being "nonresponders" the hepatitis B antigen.

The immunization protocol is the same as that in Example 2.

The results obtained are indicated in Table 1 below; this includes the number of mice which have undergone seroconversion, after the booster injection, in each of the groups tested.

For this test, it is considered that there is seroconversion when the levels of antibodies induced are detectable during ELISA assay.

TABLE 1

| MOUSE GROUP | NUMBER OF "RESPONDERS" |
| --- | --- |
| Hbs antigen alone | 1/8 |
| Ag + Al hydroxide | 0/8 |
| Ag + prior art adjuvant | 0/8 |
| Ag + DC-chol | 5/8 |

The results obtained show the efficacy of the subject of the invention which makes it possible to increase the level of seroconversion and therefore to reduce the number of "nonresponding" subjects during immunization against a highly purified antigen.

What is claimed is:

1. A method of inducing an immune response to a subunit antigen in a non-responding subject, the method comprising administering to the subject a composition comprising the subunit antigen and an amphipathic compound.

2. The method according to claim 1, wherein said antigen is a hepatitis B antigen.

3. The method according to claim 1, wherein the amphipathic compound is DC-chol.

4. The method according to claim 2, wherein the amphipathic compound is DC-chol.

5. The method according to claim 1, wherein the composition is multivalent.

6. The method according to claim 2, wherein the composition is multivalent.

7. The method according to claim 3, wherein the composition is multivalent.

8. The method according to claim 1, wherein the amphipathic compound is in the form of a dispersion in an aqueous or oily medium.

9. The method according to claim 3, wherein the DC-chol is in the form of a dispersion in an aqueous or oily medium.

10. The method according to claim 1, wherein the amphipathic compound is in a freeze-dried formulation.

11. The method according to claim 3, wherein the DC-chol is in a freeze-dried formulation.

12. The method according to claim 1, wherein the composition further comprises an adjuvant.

13. A vaccine composition comprising a hepatitis B antigen and DC-chol.

* * * * *